United States Patent [19]
Lakah et al.

[11] 4,078,082
[45] * Mar. 7, 1978

[54] MUCOLYTICALLY EFFECTIVE AGENTS

[75] Inventors: Lucien Lakah; Gabriel Maillard, both of Paris; Maurice Joullié, Yvelines; Christian Jean Marie Warolin, Paris, all of France

[73] Assignee: S.A. Joullie International, Neuilly-sur-Seine, France

[*] Notice: The portion of the term of this patent subsequent to Mar. 7, 1995, has been disclaimed.

[21] Appl. No.: 731,555

[22] Filed: Oct. 12, 1976

Related U.S. Application Data

[63] Continuation-in-part of Ser. No. 631,126, Nov. 11, 1975, abandoned.

[30] Foreign Application Priority Data

Nov. 13, 1974 France .............................. 74 37397

[51] Int. Cl.$^2$ ............................................. A61K 31/19
[52] U.S. Cl. ................................................ 424/317
[58] Field of Search ..................... 424/317; 260/526 S

[56] References Cited

U.S. PATENT DOCUMENTS

| | | | |
|---|---|---|---|
| 2,397,976 | 4/1946 | O'Leary | 260/398.5 |
| 2,449,992 | 9/1948 | Gresham et al. | 260/526 S |
| 3,109,777 | 11/1963 | Zviak | 424/315 |

FOREIGN PATENT DOCUMENTS 539,330  11/1931  Germany.

OTHER PUBLICATIONS

Sahasrabudhe, Chemical Abstracts 67:115647s, (1967).
Rabinovich et al., Chemical Abstracts 58:1341h, (1963).
Solladie-Cavallo et al., Chemical Abstracts 66:115269z, (1967).
Deichmann et al., Chemical Abstracts 43:1867e, (1949).
Walker, Chemical Abstracts 59:1435f, (1963).
Schoberl et al., Chemical Abstracts 42:7711i, (1948).
Challenger et al., Chemical Abstracts 53:16949h, (1959).

*Primary Examiner*—Leonard Schenkman
*Attorney, Agent, or Firm*—Stevens, Davis, Miller & Mosher

[57] ABSTRACT (Carboxyalkylthio)acetic acid and their salts provide a mucolytic effect, and the calcium and magnesium salts are of a special interest for the field of immune response reactions.

11 Claims, No Drawings

MUCOLYTICALLY EFFECTIVE AGENTS

RELATION TO PARENT APPLICATION

This application is a continuation-in-part of Ser. No. 631,126, filed Nov. 11, 1975, now abandoned

BACKGROUND OF THE INVENTION

The present invention relates to pharmaceutical compositions, in particular to compositions containing an active ingredient having mucolytic or mucoregulating properties.

Carboxymethylthio acetic acid has been tested in rats against cancer by M.B. SAHASRABUDHE (Chemical Abstracts 67, 115647s (1967)).

Some of the acids and salts of carboxy alkylthio acetic acids of the formula $$HOOC-(CH_2)_n-S-CH_2-COOH \qquad (I)$$

in which $n$ is 1 to 5 are known.

The acids of the above formula (I) and some salts are known per se and may be prepared by known processes. Thus, the preparation of acids in which $n$ is 1, 2, or 3 is described by the following authors : N. Hellström, Zeitschr. Physik. Chim. (A), 157, 249 (1931), 163, 37, (1933); Larsson and Jönsson, Ber, 67, 759 (1934) and E. A. Fehnel, J. Am. Chem. Soc., 74, 1569-74 (1952). A synthetic route consists of reacting mercapto acetic acid with a halogenated carboxylic acid of the formula:

$$X-(CH_2)_n-COOH$$

wherein X represents a halogen atom such as chlorine, bromine or iodine and $n$ is 1, 2 or 3.

In practice a derivative of the appropriate halogenated carboxylic acid such as an alkali metal salt or an ester, in aqueous alkaline solution, or in absolute alcohol in the presence of sodium ethanolate is used. The temperature employed may be of the order of 25° C for 30 to 60 minutes, followed by heating of the reaction mixture under reflux for one hour. Where the reaction product is a salt or ester the free acid can be obtained by conventional methods using an acid such as hydrochloric acid or sulphuric acid. The yields are usually of the order of 70 to 80%.

Certain compounds can be characterised as:

(Carboxymethylthio)acetic acid HOOC—CH$_2$—S—CH$_2$—COOH, called compound LJ 638 hereinafter, melting at 129°–130° C. This compound is outside the scope of the present invention.

(Carboxyethylthio)acetic acid HOOC—CH$_2$—CH$_2$—S—CH$_2$—COOH, called compound LJ 629 hereinafter, melting at 94° C.

(Carboxypropylthio)acetic acid HOOC—CH$_2$—CH$_2$—CH$_2$—S—CH$_2$—COOH, called compound LJ 630 hereinafter, melting at 74° C.

(Carboxybutylthio)acetic acid HOOC—(CH$_2$)$_4$—S—CH$_2$—COOH, of which the preparation is described by M. S. Rabinovich et al. Zh. Obshch. Khim. 32, 1167-72 (1972), melting at 57° C.

(Carboxypentylthio)acetic acid HOOC—(CH$_2$)$_5$—S—CH$_2$—COOH, of which the preparation is described by Horst Remane et al., J. Prakt, Chem. 312, (6), 1058-62 (1970), melting at 86° C.

SUMMARY OF THE INVENTION

In a first aspect, this invention relates to pharmaceutical compositions of (carboxyalkylthio)acetic acid and its pharmaceutically active salts, which have been found to possess a mucolytic effect in mammalian tests, indicating their use in mammals, including humans. By a mucolytic effect is contemplated a decrease in the viscosity of mucous secretions. The invention may thus also be described as providing a mucoregulatory effect.

While this invention is intended to cover the regulation of mucous secretions of mammals generally, it should be noted that tests have shown the particular suitability of the instant pharmaceutical compositions for decreasing the viscosity of mucous in the respiratory tract. Accordingly, it is seen that in accordance with a preferred embodiment, the pharmaceutical compositions of the invention are used for the treatment of bronchopulmonary disorders requiring a muocolytic agent.

The (carboxyalkylthio)acetic acid compounds of the invention (IA) may be defined by the formula (I) wherein $n$ is an integer of from 2 to 5.

A typical pharmaceutically acceptable salt form is the sodium salt form.

Although the active ingredient of the pharmaceutically effective ingredient of the above composition may be delivered orally, nasally, by suppository or injection, the pharmaceutical compositions of this first aspect of the invention are suitable for oral, nasal or suppository delivery to the patient.

The pharmaceutical compositions of the present invention comprise a mucolytically effective amount of (carboxyalkylthio)acetic acid (IA) in association with a pharmaceutically acceptable carrier (vehicle). As a pharmaceutically effective amount a daily dosage of at least about 3 milligrams per kilogram should be administered to a patient to provide a mucolytic effect, with a range of 3 to 60 milligrams per kilogram bodyweight being suggested as a starting point, with a daily dosage for infants starting from the reference dosage of 3 mg/kg. For adults, a preferred range is 3 to 10 milligrams per kg bodyweight. A mean daily therapeutic dosage for man is from about 0.2 to about 4.0 grams, or in accordance with a preferred embodiment from 0.200 to 0.600 gram.

From oral administration the pharmaceutically acceptable carrier may be, for example, starch in association with a sweetening agent such as saccharose.

In accordance with a second aspect of the invention, there is provided a method of providing a mucolytic agent to a patient which comprises administering to said patient a mucolytically effect amount of (carboxyalkylthio)acetic acid (IA) through oral, nasal, suppository or injection method, with one embodiment of the invention comprising the delivery of the drug by oral, nasal or suppository route.

In a third aspect of the invention there are provided certain salt forms of (carboxyalkthio)acetic acid (IA) specifically the salts calcium (carboxyalkythio)acetate and magnesium (carboxyalkythio)acetate, which are useful both in accordance with the first two aspects of this invention but also are of interest for immune response reactions.

DETAILED DESCRIPTION OF THE INVENTION

The following pharmacological studies using the (carboxyalkylthio)acetic acid illustrates their properties.

EXAMPLE I

The lethal dose after oral administration (LD50 and LD100) was determined for 25 grams Swiss EOPS NMRI Han ♂ mice by the method of Karber and Behrens (Arch. Exp. Pathol. Pharm 177, 1935, page 379), and the results obtained are given in Table 1 below.

TABLE 1

LD 0 = Lethal dose 0 – maximum dose tolerated
LD 50 = Lethal dose 50
LD 100 = Lethal dose 100 – minimum dose all dead.

| Compound | Dose in g/kg | | |
|---|---|---|---|
| | LD 0 | LD 50 | LD 100 |
| LJ 629 n = 2 | 2 | 2,9 | 5 |
| LJ 630 n = 3 | 3 | 3,7 | 5 |

EXAMPLE II

Action on the Bronchial Epithelium and its Secretion

To produce experimentally a bronchial hypersecretion, 200 grams female rats are submitted in an airtight cage to a daily inhalation of $SO_2$ at a concentration of 300 ppm, 2 to 5 hours per day and for 5 days a week.

After 110 hours of the inhalation environment, endobronchitic retention of mucous is observed.

The animals are killed by sections through the abdominal aorta under nembutal anaesthesia. For the quantitative determination of the mucous secretion in different groups of animal, the left lung is rapidly fixed in formaldehyde and in alcohol and then along the principle bronchi after endotracheal colouration with blue alcian.

The bronchi is examined under a microscope in aqueous medium and for each lung the presence or absence of bronchial retention as well as its appearance [solid plugs, nodular clusters, vascular vesicles (blistery clusters) etc...] is noted.

For qualitative examination, the same lung is fixed in Dubosq-Brasil liquid, enclosed in paraffin and cut such that it is possible spread out on a histological slide the entire bronchial tree, principle bronchi with four branches.

Two methods of colouration were used:

(a) The technique of Hotchkiss-MacManus with SPA (Schiff periodic acid) to show the mucines in the calciform cells.

(b) The technique of Barrnett and Seligman with DDD (2,2'-dihydroxy-6,6'-dinaphtyl disulphide) for the detection of thiol groupings in the bronchial mucous.

Forty five 200 grams female rats were submitted to repeated inhalation of $SO_2$, according to the technique described above. After 80 hours exposure to the irritant gas, 5 rats were killed and examined to verify bronchial hypersecretion.

At this time, the remaining 40 animals were separated into four groups of 10 animals each and all were submitted to inhalation sessions. For this period the animals received each day for 16 consecutive days the following treatments:

| Group 1 : 1 ml distilled water | |
|---|---|
| Group 2 : LJ 629 | |
| Group 3 : LJ 630 | 100 mg/kg p.o. in 1 ml volume |
| Group 4 : LJ 638 | |

At the end of the experiment the total duration of exposure to $SO_2$ was 110 hours.

The number of animals (out of 10 per each group) showing endobronchial retention of mucous is shown in the following Table 2:

TABLE 2

| Group 1 | (control $SO_2$ alone) | 8/10 |
|---|---|---|
| Group 2 | (LJ 629) | 3/10 |
| Group 3 | (LJ 630) | 2/10 |
| Group 4 | (LJ 638) | 1/10. |

Also with the three compounds studied (that is for Groups 2 to 4) it was observed that there was a diminution of caliciform hyperplasy shown by SPA colouration.

In addition to the bronchial mucous, it was observed that there was a disappearance of SH groupings in the control group 1 irritated with $SO_2$ but not in the groups treated with the compounds used in the present invention.

It follows from the above that the mercapto acetic acid derivatives used in the present invention act favourably on the secretion of the bronchial epithelium in returning to normal the quantity of mucous produced and restoring the biochemical equilibrium of the perturbed bronchial wall.

The compounds of the invention as a result of their mucolytic and mucoregulatory properties may be used in the treatment of infections of the respiratory mucous and in the treatment of secretory disorders (hyperviscosity).

Their use is indicated in pneumology and E.N.T. in infections where their action on the respiratory mucous cell and on the secretions of this mucous (mucolysis-mucoregulation) constitutes the essential part of the therapeutic action.

The principle indications are:

In Pneumology — in accute and chronic bronchitis, infectious chronic obstructive bronchopathy, toxic manifestations due to the inhalation of harmful atmospheres or otherwise, bronchorrhoea, emphysemia, tracheobronchitis, and as an adjuvant to treatment for assisting respiration (respiratory re-animation), In E.N.T. — in chronic otitis, chronic sinusitis, pharyngitis and rhinopharyngitis, tubular catarrh and in the preparation for E.N.T. operations.

The invention thus includes a method of treating an animal, including man, to achieve a mucolytic or mucoregulating effect, which method comprises administering to the animal of the above formula I or a pharmaceutically acceptable salt thereof.

Typically, the compound or salt may be administered in a composition in accordance with the invention.

EXAMPLE III

A tablet suitable for oral administration is prepared with 0.200 g (carboxyethylthio)acetic acid, 0.100 g saccharose, 0.005 g colloidal silica, 0.040 g starch, 0.005 g magnesium stearate to produce a tablet with 0.350 g.

EXAMPLE IV

By substituting for (carboxyethylthio)acetic acid an equivalent amount of (carboxypropylthio)acetic acid in the formulation of Example III, an alternative formulation of a tablet of the invention may be obtained.

EXAMPLE V

A mucolytically effective syrup may be prepared through the mixture of 0.500 g (carboxyethylthio)acetic acid, 70 g saccharose, 0.15 g methyl-p-hydroxybenzoate, perfume q.s. and distilled water q.s.p. 100 ml.

EXAMPLE VI

A mucolytically effective syrup may be made by following the instructions of Example V, but substituting (carboxypropylthio)acetic acid for (carboxyethylthio)acetic acid in an equivalent amount.

EXAMPLES VII and VIII

Suppositories suitable for rectal administration are prepared through the formulation of 0.200 g of either (carboxyethylthio)acetic acid (Example VII) or (carboxypropylthio)acetic acid (Example VIII) with:
Semi-synthetic glycerides q.s.p.
1 suppository of 2 g.

EXAMPLES IX–XII

By selection of the appropriate acid (IA) and treating it with either calcium hydroxide or magnesium carbonate or hydroxide, the following salts are obtained.

| EXAMPLE | SALT |
|---|---|
| IX | Magnesium (carboxyethylthio)acetate |
| X | Magnesium (carboxypropylthio)acetate |
| XI | Calcium (carboxyethylthio)acetate |
| XII | Calcium (carboxypropylthio)acetate. |

EXAMPLE XIII

All of the salts of Examples IX to XII are of interest for properties which may differ from the sodium salt outside the field of mucolytic activity. Particularly, these salts have been investigated for immune response.

The following experimental tests are the basis for this statement.

The stimulating or inhibitory action of magnesium (carboxyethylthio)acetic — called LJ 1164 hereafter — has been investigated in humoral response on the one hand and cellular response on the other hand.

Humoral response was treated by administring lipopolysaccharide (LPS) according to the method of VUJANOVIC, LE BOUTEILLER et al. (Ann. Immunol. 125, 532 (1974), C.R.Acad. Sc. Paris 277, serie D, 901 (1973)), who showed that LPS increases the number of cells having medullary aspect.

Cellular response was treated by administering oxazolone according to the method of TURK (In delayed hyposensitivity, North Holland Publ., 138 (1967)) and ANDERSON et al. (Cell. Immunol. 4, 138 (1972)), who showed that the response to oxazolone is related particularly to T cells.

Compound LJ 1164 has been administered in aqueous solution via oral route in a daily dosage of 50 mg/kg for 10 days to male BALB/C mice of 8 weeks old.

The results obtained for humoral response induced by intraveneous LPS are given in tables 3 (A–E) below. LJ 1164 decreases substantially humoral immunity:
33% decrease of the number of antigen recognizing cells (RFC: roset forming cells)
86% decrease of the number of hemolysis plaques forming cells (PFC)
8 times decrease of the hemolysing antibodies
4 times decrease of the hemagglutining antibodies.

The results obtained for cellular response induced by oxazolone are given in tables 4 (A–E) below. LJ 1164 is active only on RFC (30% decrease). Therefore one may consider that LJ 1164 does not modify substantially cellular immunity while it has a very strong effect on humoral immunity.

TABLE 3A

Effect of LJ 1164 on immune response induced by LPS evaluated by the number of cells in the spleen.

| Day of sampling after LPS | NUMBER OF CELLS/SPLEEN | | |
|---|---|---|---|
| | CONTROLS (C) | TREATED (T) | % VARIATIONS $\frac{T-C}{C} \times 100$ |
| 5$^{th}$ | 79.7 × 10$^6$ | 65.7 × 10$^6$ | − 17.6 |
| 9$^{th}$ | 159.5 × 10$^6$ | 197.0 × 10$^6$ | + 23.5 |

TABLE 3B

Effect of LJ 1164 on immune response induced by LPS evaluated by the number of RFC

| Day of sampling after LPS | NUMBER OF RFC | | | | | |
|---|---|---|---|---|---|---|
| | FOR 10$^6$ CELLS | | | PER ORGAN | | |
| | CONTROLS (C) | TREATED (T) | % VARIATIONS $\frac{T-C}{C} \times 100$ | CONTROLS (C) | TREATED (T) | % VARIATIONS $\frac{T-C}{C} \times 100$ |
| 5$^{th}$ | 1 805 | 1 194 | − 33.9 | 143 858 | 78 445 | − 45.5 |
| 9$^{th}$ | 750 | 1 000 | + 33.3 | 119 625 | 197 000 | + 64.7 |

TABLE 3C

Effect of LJ 1164 on immune response induced by LPS evaluated by the number of PFC

| Day of sampling after LPS | NUMBER OF PFC | | | | | |
|---|---|---|---|---|---|---|
| | FOR 10$^6$ CELLS | | | PER ORGAN | | |
| | CONTROLS (C) | TREATED (T) | % VARIATIONS $\frac{T-C}{C} \times 100$ | CONTROLS (C) | TREATED (T) | % VARIATIONS $\frac{T-C}{C} \times 100$ |
| 5$^{th}$ | 263 | 35 | − 86.7 | 20 961 | 2 299 | − 89.0 |
| 9$^{th}$ | 102 | 70 | − 31.4 | 16 269 | 13 790 | − 15.2 |

TABLE 3D

Effect of LJ 1164 on immune response induced by LPS by serologic dosage of the homolysing antibodies

| Day of sampling after LPS | TITRE OF HEMOLYSING ANTIBODIES | | |
|---|---|---|---|
| | CONTROLS (C) | TREATED (T) | T/C |
| 5$^{th}$ | 10 240 = 55 × 2$^{11}$ | 1 280 = 5 × 2$^8$ | $\frac{1}{8}$ |
| 9$^{th}$ | 256 = 2$^8$ | 512 = 2$^9$ | 2 |

TABLE 3E

Effect of LJ 1164 on immune response induced by LPS by serologic dosage of the hemagglutining antibodies

| Day of sampling after LPS | TITRE OF HEMAGGLUTINING ANTIBODIES | | |
|---|---|---|---|
| | CONTROLS (C) | TREATED (T) | T/C |
| $5^{th}$ | $512 = 2^9$ | $128 = 2^7$ | $\frac{1}{2^2} = \frac{1}{4}$ |
| $9^{th}$ | $512 = 2^9$ | $512 = 2^9$ | 1 |

TABLE 4A

Effect of LJ 1164 on immune response induced by oxazolone evaluated by the number of cells of the ganglion

| Day of sampling after oxazoline | NUMBER OF CELLS/GANGLION | | |
|---|---|---|---|
| | CONTROLS (C) | TREATED (T) | % VARIATIONS $\frac{T-C}{C} \times 100$ |
| $5^{th}$ | $16.8 \times 10^6$ | $19.6 \times 10^6$ | + 16.7 |
| $9^{th}$ | $17.8 \times 10^6$ | $13.6 \times 10^6$ | − 23.6 |

TABLE 4B

Effect of LJ 1164 on immune response induced by oxazolone evaluated by the number of RFC

| | NUMBER OF RFC | | | | | |
|---|---|---|---|---|---|---|
| | FOR $10^6$ CELLS | | | PER ORGAN | | |
| Day of sampling after oxazolone | CONTROLS (C) | TREATED (T) | % VARIATIONS $\frac{T-C}{C} \times 100$ | CONTROLS (C) | TREATED (T) | % VARIATIONS $\frac{T-C}{C} \times 100$ |
| $5^{th}$ | 6 330 | 4 416 | − 30.2 | 106 344 | 86 556 | − 18.6 |
| $9^{th}$ | 9 080 | 9 746 | + 7.3 | 161 624 | 132 546 | − 18.0 |

TABLE 4C

Effect of LJ 1164 on immune response induced by oxazolone evaluated by the number of PFC

| | NUMBER OF PFC | | | | | |
|---|---|---|---|---|---|---|
| | FOR $10^6$ CELLS | | | PER ORGAN | | |
| Day of sampling after oxazolone | CONTROLS (C) | TREATED (T) | % VARIATIONS $\frac{T-C}{C} \times 100$ | CONTROLS (C) | TREATED (T) | % VARIATIONS $\frac{T-C}{C} \times 100$ |
| $5^{th}$ | 307 | 262 | − 14.6 | 5 157 | 5 135 | − 0.4 |
| $9^{th}$ | 35 | 63 | + 80.0 | 623 | 856 | + 37.4 |

TABLE 4D

Effect of LJ 1164 on immune response induced by oxazolone by serologic dosage of the hemolysing antibodies

| Day of sampling after oxazolone | TITRE OF HEMOLYSING ANTIBODIES | | |
|---|---|---|---|
| | CONTROLS (C) | TREATED (T) | T/C |
| $5^{th}$ | $40 = 5 \times 2^3$ | $40 = 5 \times 2^3$ | 1 |
| $9^{th}$ | $1\,024 = 2^{10}$ | $4\,096 = 2^{12}$ | $2^2 = 4$ |

TABLE 4E

Effect of LJ 1164 on immune response induced by oxazolone by serologic dosage of the hemagglutining antibodies

| Day of sampling after oxazolone | TITRE OF HEMAGGLUTINING ANTIBODIES | | |
|---|---|---|---|
| | CONTROLS (C) | TREATED (T) | T/C |
| $5^{th}$ | $4 = 2^2$ | $4 = 2^2$ | 1 |
| $9^{th}$ | 0 | 0 | — |

What is claim:

1. A mucolytic composition comprising a mucolytically effective amount of (carboxyalkythio)acetic acid of the formula $$HOOC—alk—S—CH_2COOH$$

wherein alk is alkylene of 3 to 5 carbon atoms in the form of the acid or pharmaceutically acceptable salt thereof and a pharmaceutically compatible carrier therefor said composition being in the form of a suppository, tablet or syrup.

2. A mucolytic composition of claim 1 wherein said mucolytically effective amount is based on a daily dosage of 3 to 60 mg per kg bodyweight.

3. A mucolytic composition of claim 2 which is a suppository.

4. A mucolytic composition of claim 3 which is tablet.

5. A mucolytic composition of claim 3 which is a syrup for oral administration.

6. A mucolytic composition of claim 2 wherein alk is propylene.

7. A method of providing a mucolytic effect to a patient having a disorder requiring a mucolytic effect which comprises administering to said patient a mucolytically effective amount of (carboxyalkythio)acetic acid of the formula HOOC—alk—S—CH₂COOH or pharmaceutically acceptable salt thereof, wherein alk is an alkylene group of 2 to 5 carbon atoms.

8. A method of claim 7 which comprises administering to said patient a daily dosage of from 3 to 60 mg per kilogram bodyweight.

9. A method of claim 8 wherein alk is ethylene.

10. A method of claim 8 wherein alk is propylene.

11. A method of claim 7 wherein said salt is the calcium or magnesium salt of a (carboxyalkylthio)acetic acid wherein the alkylene groups is of 2 to 5 carbon atoms.

* * * * *